(12) United States Patent
Sobti et al.

(10) Patent No.: US 10,828,205 B2
(45) Date of Patent: Nov. 10, 2020

(54) REMOTE DETECTION OF WETNESS IN DIAPERS AND BANDAGES USING REUSABLE ELECTRONICS

(71) Applicants: Arun Sobti, South Barrington, IL (US); Pamela Sobti, South Barrington, IL (US); Raj Panchal, South Barrington, IL (US); Darshana Panchal, South Barrington, IL (US)

(72) Inventors: Arun Sobti, South Barrington, IL (US); Pamela Sobti, South Barrington, IL (US); Raj Panchal, South Barrington, IL (US); Darshana Panchal, South Barrington, IL (US)

(73) Assignee: S-SQUARE SYSTEMS, LLC, South Barrington, IL (US)

( * ) Notice: Subject to any disclaimer, the term of this patent is extended or adjusted under 35 U.S.C. 154(b) by 0 days.

(21) Appl. No.: 16/209,576

(22) Filed: Dec. 4, 2018

(65) Prior Publication Data

US 2019/0167488 A1  Jun. 6, 2019

Related U.S. Application Data

(60) Provisional application No. 62/594,864, filed on Dec. 5, 2017.

(51) Int. Cl.
G08B 21/00 (2006.01)
A61F 13/42 (2006.01)
G08B 21/20 (2006.01)

(52) U.S. Cl.
CPC .............. *A61F 13/42* (2013.01); *G08B 21/20* (2013.01); *A61F 2013/424* (2013.01); *A61F 2013/429* (2013.01)

(58) Field of Classification Search
None
See application file for complete search history.

(56) References Cited

U.S. PATENT DOCUMENTS

| | | | | |
|---|---|---|---|---|
| 6,097,297 A | * | 8/2000 | Fard | A61F 13/42 128/886 |
| 6,725,075 B2 | * | 4/2004 | Al-Ali | A61B 5/14552 600/323 |
| 6,950,687 B2 | * | 9/2005 | Al-Ali | A61B 5/14552 600/310 |
| 7,039,449 B2 | * | 5/2006 | Al-Ali | A61B 5/14552 600/310 |

(Continued)

*Primary Examiner* — Julie B Lieu

(57) ABSTRACT

A re-usable electronics device is detachably coupled with a harness physically connected with an article whose wetness condition is to be detected. The harness comprises a set of first conductors, and the re-usable electronics device comprises a set of second conductors on its outer surface such that when the re-usable electronics device is operatively coupled with the harness by insertion in a pouch of the harness, the set of first conductors make electrical contact with the set of second conductors enabling detection of change in voltage across at least one pair of the first conductor above a threshold value. The change in the voltage occurs due to change in resistance of resistance based wetness sensors configured with the harness and operatively coupled to the set of first conductors. Upon detection of the change, the device transmits a notification indicating wetness of the article.

18 Claims, 7 Drawing Sheets

(56) References Cited

U.S. PATENT DOCUMENTS

| | | | | |
|---|---|---|---|---|
| 7,489,252 | B2* | 2/2009 | Long | A61F 13/42 |
| | | | | 340/573.5 |
| 7,595,734 | B2* | 9/2009 | Long | A61F 13/42 |
| | | | | 340/573.5 |
| 7,734,320 | B2* | 6/2010 | Al-Ali | A61B 5/14552 |
| | | | | 600/310 |
| 8,000,761 | B2* | 8/2011 | Al-Ali | A61B 5/14552 |
| | | | | 600/310 |
| 8,273,939 | B2* | 9/2012 | Klofta | A61F 13/42 |
| | | | | 604/361 |
| 9,107,776 | B2* | 8/2015 | Bergman | A61F 13/42 |
| 9,386,953 | B2* | 7/2016 | Al-Ali | A61B 5/14552 |
| 2012/0157947 | A1* | 6/2012 | Nhan | A61F 13/42 |
| | | | | 604/361 |
| 2016/0008182 | A1* | 1/2016 | Prokopuk | A61F 13/42 |
| | | | | 604/361 |
| 2017/0202502 | A1* | 7/2017 | Cretu-Petra | A61B 5/208 |
| 2018/0177644 | A1* | 6/2018 | Tuli | A61F 13/42 |
| 2018/0325743 | A1* | 11/2018 | Ho | A61F 13/42 |

* cited by examiner

REMOTE DETECTION OF WETNESS IN DIAPERS AND BANDAGES USING REUSABLE ELECTRONICS

CROSS REFERENCE TO RELATED APPLICATION

This application claims the benefit of U.S. Provisional Patent Application No. 62/594,864 filed on Dec. 5, 2017, the contents of which, in its entirety, is herein incorporated by reference.

BACKGROUND

Technical Field

The embodiments herein generally relate to monitoring of wetness of articles such as a diaper, a bandage, or a sanitary napkin; and more particularly to a reusable electronic device that enables remote monitoring of condition of the articles.

Description of the Related Art

Remote monitoring of articles like diapers, bandages, and sanitary napkins, to ensure that they are changed timely, has been in vogue for quite some time. Monitoring is typically based on sensors that are embedded into the diapers or added onto the article to be monitored. Such monitoring means are single use items to be discarded along with the article. A few reusable devices, which have been disclosed in the art, integrate wetness sensors that come in contact with body fluid, and therefore, are undesirable from hygiene point of view.

Considering wide acceptance of remote monitoring of articles such as a diaper, a bandage, or a sanitary napkin, there is a need of an improved reusable device for remote monitoring of wetness that takes care of above concern, thereby providing an acceptable and cost effective solution to remote monitoring of wetness.

SUMMARY

In view of the foregoing, an embodiment herein provides a re-usable electronics device that can be detachably coupled with a harness, which is physical coupled with an article whose wetness condition is to be detected. The harness includes a set of first conductors, and the re-usable electronics device includes a set of second conductors configured on outer surface of the electronic device such that when the re-usable electronics device is operatively coupled with the harness, the set of first conductors make electrical contact with the set of second conductors such that change in voltage across at least one pair of first conductors above a threshold value is detected by the electronic device to transmit a notification indicating wetness of said article.

In an aspect, the harness may comprise a pouch in which said device is positioned, and the set of first conductors may be configured on at least one inner side of the pouch.

In an aspect, the first conductors of the at least one pair of first conductors may be located on opposite inner sides of the pouch, and likewise the second conductors of a pair of second conductors of the device with which the pair of first conductors make contact, may be located on opposite sides of the device.

In an aspect, said article is selected from any or a combination of a diaper, a sanitary napkin, and a bandage.

The harness comprises one or more legs extending from the pouch. The one or more legs may be positioned at different locations in the article for sensing wetness of the article at different locations, while the pouch is located away from locations likely to get wet to prevent soiling of the device. For example, when the article is a diaper, a first leg may be positioned at rear side of the diaper to detect wetness due to poop, and a second leg may be positioned at front side of the diaper to detect wetness due to urine. Alternatively, both the legs may run from front side of the diaper to rear side of the diaper to detect any of urine and poop related event or incrementally both as different thresholds of wetness are crossed.

In an aspect, the harness may be made of any or a combination of a fabric, and a paper that is embedded with at least one pair of conductive path connected to the at least one pair of first conductors. The conductive paths may be provided by painting the at least one leg with conductive material, such as but not limited to, silver ink. In an example implementation, the two conductive paths of the at least one pair of conductive path may be configured on two opposite sides of the at least one leg.

The conductive paths belonging to the at least one pair of conductive path provided on the at least one leg may be connected to two ends of a wetness sensor, thereby connecting the wetness sensor to the at least one pair of first conductors.

In an aspect, the wetness sensor, upon detecting wetness of the article beyond a defined limit, is configured to enable change in voltage across the corresponding pair of first conductors, said change in voltage being greater than said threshold value.

In an aspect, the wetness sensor may be a wetness-based resistor. In an implementation, the entire conductive path may work as wetness sensor, and the two conductive paths painted on two opposite sides of a leg may be electrically connected to each other using a conductive cap at end of the leg.

In an aspect, the device may incorporate a visual indicator that is configured to indicate that the electrical contact between the set of first conductors and the set of second conductors has been established.

In an aspect, said notification may be transmitted by said re-usable electronics device to a remotely located computing device, said computing device being selected from any or a combination of a mobile phone, a smart phone, a laptop, a desktop PC, a server, and a wirelessly connected computing device.

In an aspect, there may be four wetness sensors such that when the set of first conductors and the set of second conductors establish the electrical contact, the four wetness sensors are configured as four sides of a Wheatstone bridge that is enabled by the device. The Wheatstone bridge enables detection of change in voltage on account of change in resistance of any one of the four wetness sensors.

In an aspect, upon issuance of the notification, the device is detached from said harness for reuse with a fresh harness that is coupled to a second article.

In an aspect, the notification issued by the device may include indications for any or a combination of wetness of said article, timestamp of said notification, whether said article is soiled, dryness of said article, level of wetness of said article, and other conditions of said article.

In an aspect, the harness may include at least one piezo electric material that when compressed changes capacitance or resistance or frequency of a signal passing through it, based on which the voltage across the at least a first conductor of the first set of conductors and the at least a corresponding second conductor of the second set of conductors changes so as to enable the device to transmit the notification when the voltage change is above the threshold value.

An aspect of the present disclosure provided a harness for physically configuring with an article whose wetness is to be measured. The proposed harness is configured to hold a re-usable electronics device that is detachably coupled thereto. In an aspect, the harness includes a set of first conductors, and the re-usable electronics device includes a set of second conductors such that when the re-usable electronics device is operatively coupled with the harness, the set of first conductors make electrical contact with the set of second conductors such that change in voltage across at least one pair of first conductor of the set of first conductors above a threshold value transmits a notification indicating wetness of the article with which the harness is physically coupled.

Another aspect of the present disclosure provides a method for remotely monitoring wetness of an article. The proposed method comprises the steps of: (i) providing a harness having a set of first conductor configured on at least one inner side of a pouch of the harness; (ii) providing a re-usable electronic device having a set of second conductors configured on outer surface of the device; (iii) operatively coupling the device with the harness by inserting the device within a pouch of the harness such that the set of first conductors make electrical contact with the set of second conductors; and (iv) transmitting a notification indicating wetness of said article based on change in voltage across at least one pair of first conductors above a threshold value. In an aspect, the detection in change in voltage is enabled by electric contact between the set of first conductors with the set of second conductors.

In an embodiment, the method may further comprise the step of positioning one or more legs of the harness extending from the pouch at different locations in the article for sensing wetness of the article at the different locations, wherein the at least one leg comprises a wetness sensor operatively coupled to the at least one pair of first conductors through a pair of conductive path configured on the at least one leg.

In an embodiment, the method may further comprise the step of securing the pouch of the harness at position away from locations in the article that are likely to get wet.

BRIEF DESCRIPTION OF THE DRAWINGS

The embodiments herein will be better understood from the following detailed description with reference to the drawings, in which.

DETAILED DESCRIPTION

Figure 1:
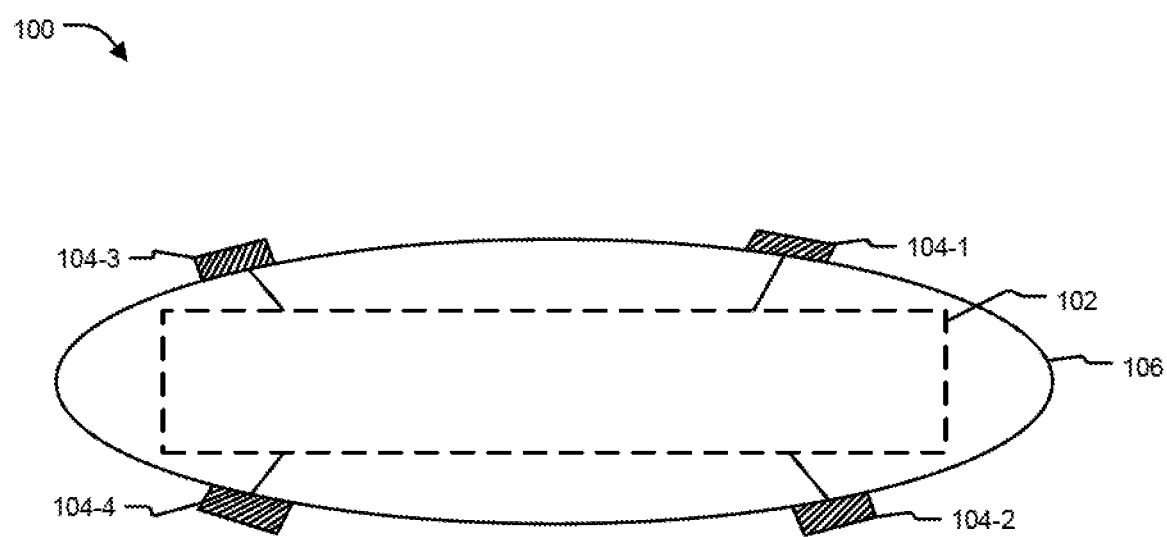
FIG. 1 is an exemplary side view of the proposed re-usable electronic device for remote monitoring of wetness of an article, according to the embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a re-usable electronic device for remote monitoring of wetness of an article such as a diaper, a bandage or a sanitary napkin, and method thereof. In an aspect, the proposed re-usable electronic device is configured for use with a harness that prevents soiling of the device thereby enabling its re-use without any concern for hygiene, while the harness can be discarded after each use.

In an embodiment, the harness may be a separate item that may be coupled with the article which is to be monitored, or may be inbuilt with the article.

In an embodiment, the re-usable electronic device (also referred to as device or pebble and the two terms used interchangeably hereinafter) may be physically coupled with the harness by inserting the device/pebble in a pouch provided in the harness, wherein insertion of the pebble in the pouch results in electrical coupling between the two. The electrical coupling enables the device to detect wet condition of the harness, which is configured with the article which is to be monitored.

In an embodiment, electrical coupling between the device/pebble and the harness is enabled by a set of first conductors configured on inner side of the pouch, and a set of second conductors configured on outer surface of the device/pebble such that when the device is inserted in the pouch, the two sets of conductors automatically come in contact with each other.

In an embodiment, the harness includes at least one leg that extends from the pouch. The legs incorporate wetness sensors that are connected between a pair of the first conductors. Therefore, when the device is electrically coupled to the pouch, the device gains access to the sensors through a pair of second conductors that make electric contact with the pair of first conductors. This enables the device to monitor wetness condition of the article where the legs of the harness may be positioned.

With the arrangement described above, the legs of the harness may be positioned at different locations of the article, where wetness condition is to be monitored, and the pouch located at a location that is not likely to get soiled. Thus, the device/pebble held within the pouch remains free from any risk of getting contaminated, enabling its re-use. In an alternate configuration, it is possible that the legs are suitably integrated with the article in an in-built fashion so as to reduce efforts required in manual positioning and orienting to the location for effective wetness detection.

In an embodiment, the harness may be made of a fabric, or paper, or a combination of the two, and the electrical connectivity between the sensor and the pair of first conductors may be enabled by painting a conductive paint, such as a silver ink, on the harness. In an embodiment, the painted conductive paint/ink itself may act, using an inkjet printer or any other means, as a resistance-based wetness sensor, wherein wetness of the ink, or wetness of part of article that lies between two conductive paths, alters the resistance between two ends of the conductive path. In such a case, conductive path created by the painted ink may terminate at the pair of first conductors. In an embodiment, the conductive path may be painted on two opposite surfaces of the leg and may be electrically coupled to each other at free end of the leg by a conductive cap provided at the free end of the leg.

In an embodiment, the harness may incorporate four legs, each configured with a resistance based wetness sensor, and the set of first conductors configured in the pouch may be four in numbers, the four resistance based wetness sensors may be connected to the four first conductors such that the four sensors are configured as four sides of a rectangle having four apex points at the four first conductors. The configuration may be used as a Wheatstone bridge such that a voltage may be applied across a first pair of first conductors located at diagonally opposite apexes of the rectangle, and resultant voltage may be measured across a second pair of the remaining two first conductors. As known in the art, the voltage applied across the first pair of first conductors remaining same, any change in resistance of any one of the four resistance-based wetness sensors shall be reflected as change in voltage across the second pair of first conductors.

In an embodiment, the device may comprise a processor, a power storage means, such as a battery, the set of second conductors working as input-output to the processor, a transceiver to transmit notification about condition of the article to a remote host, a reset button to reset the processor to capture reference voltage value indicating dry condition of the article, and a visual indicator configured to indicate, on the device being inserted within the pouch, that electrical contact between the set of first conductors and the set of second conductors has been established.

In an embodiment, the device, in its sleep mode, may be configured to periodically detect if set of second conductors of the device has established electrical contact with the set of first conductors on the pouch of a harness. If it is found that contact has been established, the processor may be woken up from the sleep mode, and the visual indicator may be turned on to indicate to a user/caregiver that device is now in working condition.

Simultaneously, the device may apply a predefined voltage across the first pair first conductors through the corresponding pair (referred to as first pair) of the second conductors, and record voltage across a pair (referred to as second pair) of second conductors that are in contact with the second pair of first conductors. The recorded voltage value may be used as reference voltage indicative of dry condition of the article.

Thereafter, the device may continuously, or periodically, apply the predefined voltage across the first pair of first conductors, and check if change in voltage across the second pair of second conductors over the reference value exceeds a predefined threshold value. If the change is less than the threshold value, periodic checking may continue, and on the other hand, if the change is voltage is found to be more than the threshold value, an alert is sent to a remote host using the transceiver.

In an embodiment, the device may continue to periodically check voltage across the first pair of second conductors and send notifications if the voltage difference is found to be beyond the threshold value. On getting the notifications, the user/caregiver may attend to the requirement of changing the article, which would include removal of the device from the pouch. Once the device has been taken out of the pouch, the detected voltage would be zero, in which case the device may go back to sleep mode.

In an embodiment, the device may be calibrated to indicate extent of wetness, wherein calibration may be done by recording voltage across the second pair of first conductors when the article is dry, and recording the voltage again after soaking the article in water. The difference between the two extreme values may be stored in the host and used to indicate extent of wetness.

It is to be appreciated that though various embodiments have been explained here with reference to remote monitoring of wetness of an article, such as a diaper, bandage or a sanitary napkin, by means of wetness sensors, the concept of a reusable device which incorporates sensor electronics and couples with a pouch can be used for many other applications beyond wetness monitoring. For example, the disclosed concept of a harness having a pouch and a pebble/device incorporating sensor electronics that operatively couples with the pouch may be used for remote monitoring changes in values including—temperature, pressure, acceleration limits, and cadence to name a few.

Referring to FIG. 1, where an example of a side view of the proposed re-usable electronic device for remote monitoring of wetness of an article is shown, the device 100 includes a printed circuit (PC) board 102 housed with a casing 106. The PC board may incorporate sensor electronics embodied within a processor, and other functional modules such as transceiver, memory etc. Other modules such as power storage etc. may also be housed within the casing 106 in appropriate manner. Outer surface of the casing 106 may be configured with a plurality of conducting tabs, referred to as second conductors, such as second conductors 104-1, 104-2, 104-3 and 104-4 (collectively referred to as 104), that project out of the outer surface of the device 100. As shown, the second conductors 104 may be operatively coupled to the PC board 102 and work as input-output of the processor configured within the PC board 102.

It is to be appreciated that though the exemplary illustration of FIG. 1 shows the tabs/second conductors 104 configured on both sides of the device/pebble 100, it is possible to have the tabs/second conductors 104 only on one side depending on shape of the device 100, configuration, including flexibility, of the pouch, and all such variations are well within the scope of the present disclosure without any limitations whatsoever.

Figure 2A:
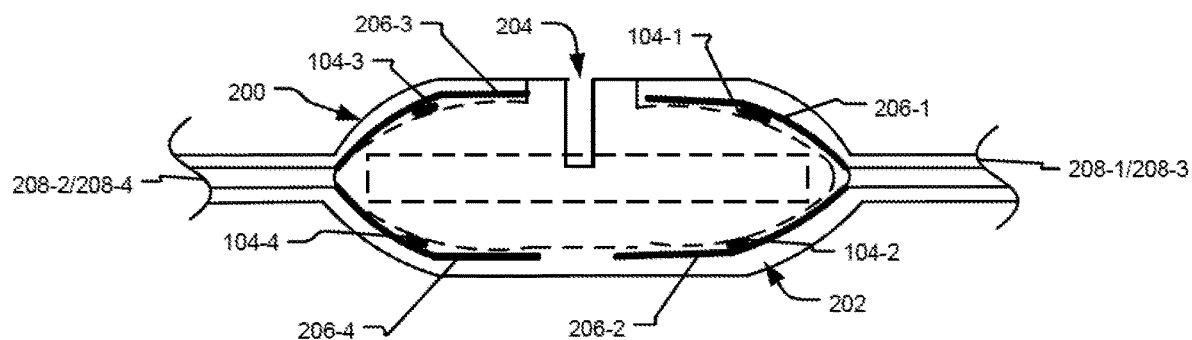
FIGS. 2A and 2B are exemplary side and top views respectively of the proposed harness having pouch and legs, along with the re-usable electronic device inserted within the pouch, according to the embodiments herein.
Figure 2B:
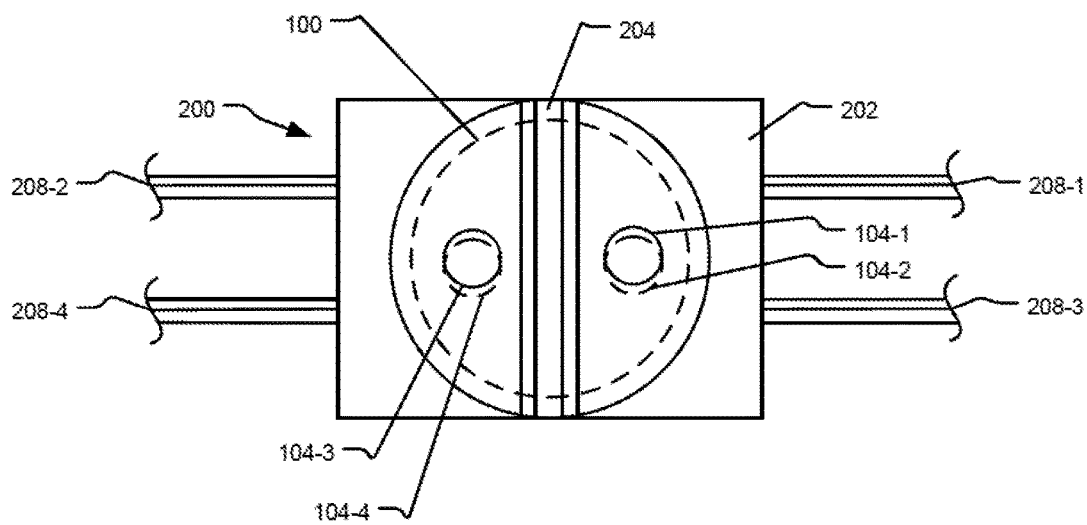

FIGS. 2A and 2B, with reference to FIG. 1, show side and top views respectively of the proposed harness, along with the re-usable electronic device 100 physically coupled with the harness. The harness 200 includes a pouch 202 having a slit 204 for physical coupling of the device 100 with the harness 200 by insertion of the device 100 within the pouch 202. The harness 200 also includes one or more legs, such as legs 208-1 and 208-2 (collectively referred to as legs 208), that are physically coupled to the pouch 202 at their one end such that they extend outward from the pouch 202.

In an aspect, inner sides of the pouch 202 are configured with a set of first conductors, such as first conductors 206-1, 206-2, 206-3 and 206-4 (collectively referred to as first conductors 206) such that when the device 100 is held within the pouch 202, the set of second conductors 104 configured on the device 100 come in contact with the set of first conductors 206 configured on inner side of the pouch 202, establishing electrical coupling of the device 100 with the harness 200.

It is to be appreciated that though the exemplary illustrations of FIGS. 2A and 2B show the harness 200 having four legs 208, it is possible to have any number of legs—lesser or more—without any limitation. For example, there may be just one leg 208, and accordingly the pouch 202 and the device 100 may have just two of the first conductors 206 and the second conductors 104 respectively. The electronic circuit within the device 100 may be configured to cater to the given number of legs 208 and the corresponding sensors provided on the legs 208.

In an embodiment, the first conductors 206 may be configured to cover a substantial area so that contact between the set of second conductors 104 and the set of first conductors 206 is ensured. In an embodiment, the first conductors 206 may be made of flexible foils of a conducting material, and may be fixed to inner surface of sides of the pouch 202, such as by pasting. In an alternate embodiment, the first conductors 206 may be configured by painting a conducting paint, such as silver ink, on inner surface of the pouch 202.

It is to be appreciated that while embodiments described herein show the first conductors 206 configured with the pouch 202 in form of conducting surfaces, and the second conductors 104 configured on the device 100 in form of protruding conductors/pin shaped conductors, it is possible to have the second conductors 104 configured on the device 100 as surface conductors, and the first conductors 206 configured with the pouch 202 in form of protruding conductors/pin shaped conductors, or both the first conductors 206 and the second conductors 104 may be in form of surface conductors, without effecting functioning of the proposed device 100 and the harness 200. Therefore, all such variations are well within the scope of the present disclosure without any limitation whatsoever.

In an embodiment, the pouch 202 may be configured for snug fit around the device 100. The snug fit may be ensured by providing one or more elastic bands (not shown here) on the sides of the pouch 202, or by making the pouch using an elastic material.

In an embodiment, the pouch 202 and the device 100 may be shaped so that the device 100, after it has been physically coupled with the pouch 202, does not change its orientation relative to the sides of the pouch 202. This can be achieved by making the device rectangle/square/oval shaped with the pouch 202 having a matching shape.

Figure 3A:
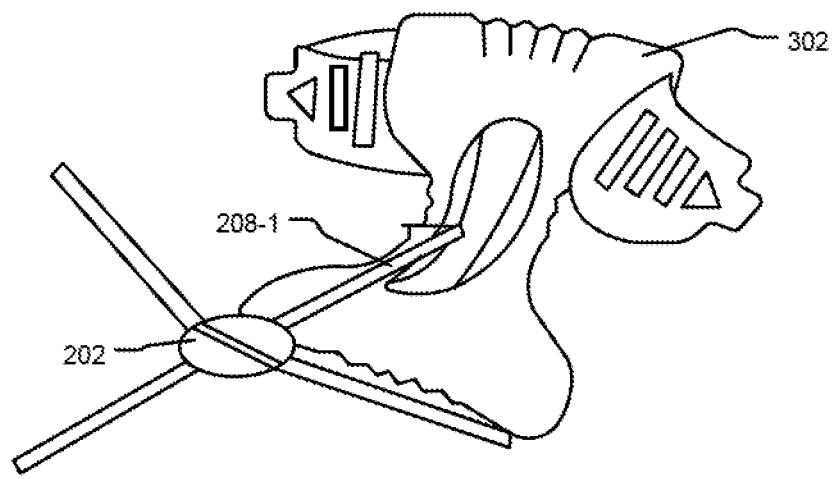
FIGS. 3A and 3B are exemplary schematic views showing use of the proposed re-usable electronic device and the harness with a diaper for remotely monitoring the condition of the diaper, according to the embodiments herein.
Figure 3B:
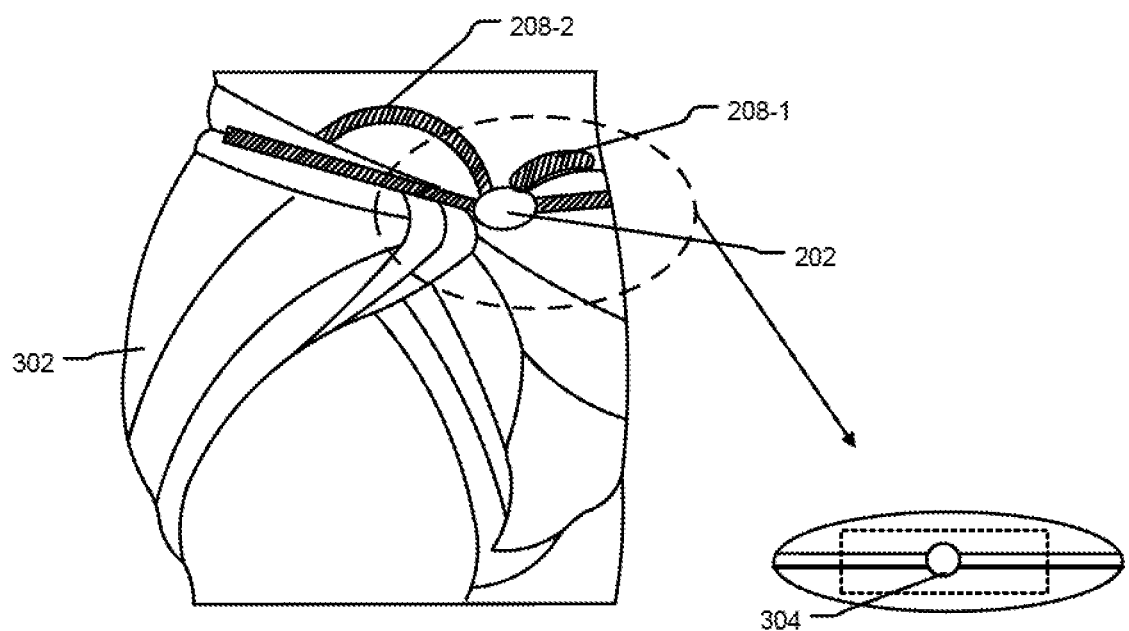

FIGS. 3A and 3B, with reference to FIGS. 1 and 2, show use of the proposed re-usable electronic device 100 and the harness 200 with a diaper for remotely monitoring the condition of the diaper 302. As shown, one of the legs, such as leg 208-1 of the harness 200 may be positioned at front side of the diaper 302 to detect wetness due to urine and another leg, such as leg 208-2 may be positioned at rear side of the diaper 302 to detect wetness due to poop. After the diaper 302 has been tied, the pouch 202 of the harness 200 may be positioned near the waist band on front side of the diaper 302 and harnessed. Thereafter, the device 100 may be inserted within the pouch 202. Once an electric coupling of the device 100 with the harness 200 is complete, a visual indicator, such as a LED 304, provided on the device 100 shall light up to indicate that the electric coupling has been established. In an embodiment, the pouch 202 may be made of a translucent material so that the visual warning is visible to the caregiver.

Figure 4A:
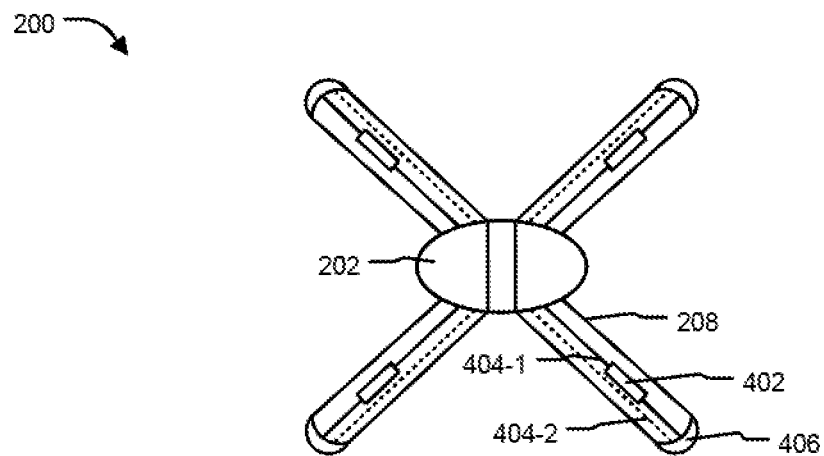
FIGS. 4A and 4B are an exemplary top view showing a harness with four legs, each leg having a resistance-based wetness sensor, and a Wheatstone bridge for detecting change in resistance of any of the four wetness sensor, according to the embodiments herein.

FIG. 4A, with reference to FIGS. 1 to 3B, shows a harness with four legs 208, wherein the harness 200 may be made of a fabric, such as but not limited to TPE, or paper, or a combination of the two, and the electrical connectivity between the sensors 402 and the pair of first conductors 206 provided in the pouch 202 by conductive paths such as 404-1 and 404-2 (collectively referred to as 404). In an embodiment, the conductive paths 404 may be created by painting a conductive paint, such as a silver ink, on the legs 208. In an embodiment, two conductive paths, such as 404-1 and 404-2, may be painted on two opposite surfaces of the legs 208, 404-1 shown in solid line being configured on upper surface and 404-2 shown in phantom line being configured on the opposite surface of the leg 208. To complete the circuit, the conductive paths 404-1 and 404-2 may be electrically coupled to each other at free end of the leg 208 by a conductive cap, such as cap 406, provided at the free end of the legs 208. Other ends of the conductive paths 404 created by the painted ink may terminate at two different first conductors 206.

In an embodiment, the painted conductive paint/ink itself may act as a resistance based wetness sensor 402, wherein wetness of the ink determines resistance of the painted ink.

In an embodiment, the harness 200 having four legs 208, each leg 208 having a resistance based wetness sensor 402, may incorporate four first conductors 206. The four resistance-based wetness sensors 402 may be connected to the four first conductors 206 such that the four sensors 402 are configured as four sides of a rectangle having four apex points at the four first conductors 206. The configuration may be used as a Wheatstone bridge, as shown in FIG. 4B, to detect any change in resistance of any one of the four resistance-based wetness sensors 402.

Figure 4B:
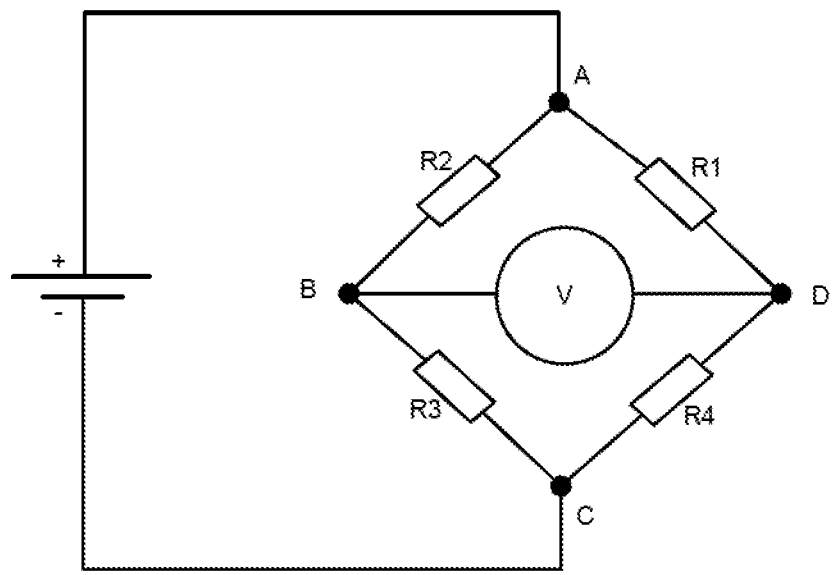

FIG. 4B with reference to FIGS. 1 to 4A shows configuration of the Wheatstone bridge formed by the four resistance-based wetness sensors 402, wherein R1, R2, R3 and R4 stand for resistances of the four resistance based wetness sensors 402 configured with four legs 208 of the harness 200, and A, B, C and D indicate four apexes of the Wheatstone bridge formed at the four first conductors 206. As shown, a known voltage may be applied diagonally opposite apexes A and C, i.e. at the first pair of first conductors 206 corresponding to apexes A and C, and resultant voltage may be measured across remaining two apexes B and D, i.e. at the second pair of first conductors 206 corresponding to apexes B and D. As known in the art, the voltage applied across the first pair of first conductors remaining same, any change in resistance of any one of the four resistance=based wetness sensors 402 shall be reflected as change in voltage across the second pair of first conductors.

Figure 5:
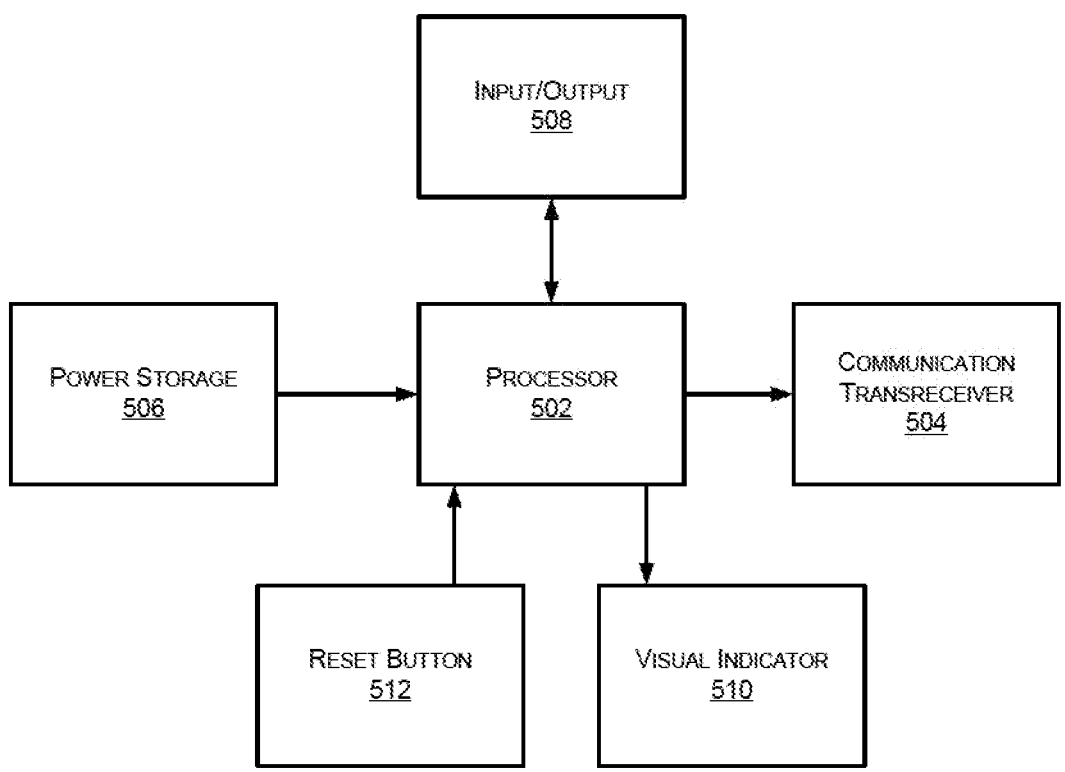
FIG. 5 is an exemplary block diagram showing different functional modules of the re-usable electronic device, according to the embodiments herein.

FIG. 5 shows different functional modules of the re-usable electronic device 100, wherein the device 100 may include a processor 502, a power storage means 506, such as a battery, input-output 508 of the device 100, a transceiver 504, a reset button 512, and a visual indicator 510.

The processor 502 may be incorporated on a PC board, such as PC board 102 shown in FIG. 1, and may be configured to execute various embedded software algorithms resulting in executing different steps involved in working of the re-usable electronic device 100.

The power storage means 506 may be a battery, such as a rechargeable battery to meet electric power requirement of the device 100, and may be located with the housing of the device 100, such as casing 106 shown in FIG. 1. In case the power storage means is a rechargeable battery, the device 100 may incorporate a charging port coupled ton the casing 106. In an embodiment, the device 100 may also incorporate a low battery charge alert, such as a visual and/or visual alert.

The input-output 508 of the device 100 work to apply a known voltage across the first pair of first conductors, and to detect voltage across the second pair of first conductors, as explained against FIGS. 4A and 4B. The set of second conductors, such as second conductors 104 shown in FIG. 1, that establish physical coupling with the first conductors 206, work as input-output 508 of the device 100.

The transceiver 504 may be located on the PC board 102 and may be operatively coupled to the processor 502 to transmit notification about condition of the article and/or about condition of the device itself, to a remote host, wherein the remote host may be located in a computing device, such as any or a combination of a mobile phone, a smart phone, a laptop, a desktop PC, a server, and a wirelessly connected IOT edge computing device.

The reset button 512 may be optionally provided on the casing 106 of the device 100 and may be operatively coupled to the processor 502. Actuating the reset button 512 may reset the processor 502 to capture the reference voltage value that is indicative of dry condition of the article. The reset button 512 may be used by user after he has replaced a soiled article with a fresh article.

The visual indicator 510 may also be provided on the casing 106 of the device 100, and as explained earlier, is configured to indicate to a caregiver, on the device 100 being inserted within the pouch, such as pouch 202 of the harness 200 as shown in FIG. 2, that electrical contact between the set of first conductors 206 and the set of second conductors 104 has been established.

Figure 6:
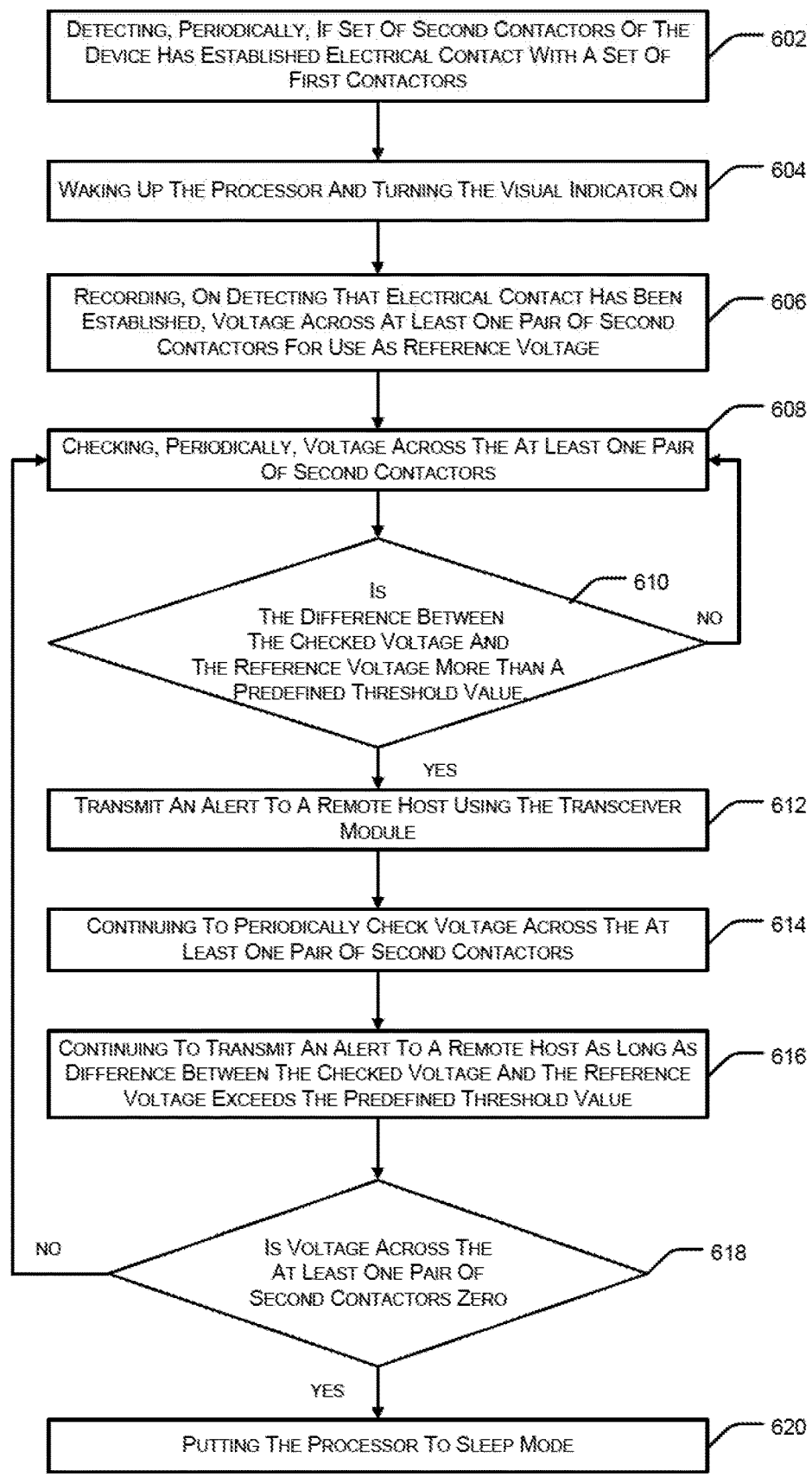
FIG. 6 is an exemplary flow diagram of working of the re-usable electronic device, according to the embodiments herein.

FIG. 6, with reference to FIGS. 1 to 5, shows various steps involved in working of the re-usable electronic device 100 for remote monitoring an article, wherein at step 602, the device 100 when it is in sleep mode, may periodically detect if set of second conductors of the device 100, such as second conductors 104 shown in FIG. 1, have established electrical contact with the set of first conductors on the pouch of a harness, such as first conductors 206 provided on the pouch 202 of the harness 200 as shown in FIG. 2.

If it is found that contact between the set of second conductors 104 and the first conductors 206 has been established, at step 604, the processor 502 may be woken up from the sleep mode, and the visual indicator, such as indicator 304 shown in FIG. 3B may be turned on to indicate to a user/caregiver that device 100 is now in working condition.

Simultaneous to the indicator 304 being turned on, at step 606, the device 100 may apply a predefined voltage across the first pair of the first conductors 206 through the corresponding pair of the second conductors 104, and record voltage across pair of second conductors 104 that are in contact with the second pair of first conductors 206. In an aspect, the recorded voltage is use as reference voltage value indicative of dry condition of the article, such as diaper 302 shown in FIGS. 3A and 3B.

As shown at step 608, the device 100 may periodically apply the predefined voltage across the first pair first conductors 206, and check, as at step 610, if change in voltage across the second pair of second conductors 104 over the reference voltage value exceeds a predefined threshold value. If the change is less than the threshold value, periodic checking may continue by going back to the step 606. On the other hand, if the change is voltage is found to be more than the threshold value, an alert is sent, as shown at step 612, to a remote host using the transceiver, such as transceiver 504 shown in FIG. 5.

In an embodiment, the device may continue to periodically check voltage across the second pair of second conductors 104, as shown at step 614, and send notifications if the voltage difference continues to be beyond the threshold value. In an embodiment, the notification may include the actual voltage value, and based on stored extreme voltage values, i.e. voltage under dry condition and voltage under condition when the article is fully soaked, the host may indicate extent of wetness.

The device 100, as shown at step 616, may continue to transmit the alert to the remote host as long as difference between the checked voltage and the reference voltage exceeds the predefined threshold value. Duration for which the device 100 continues to send notification may be exponential, self-configurable based on battery condition and computing capacity of the device 100.

On getting the notifications, the user/caregiver may attend to the requirement of changing the article, which would include removal of the device 100 from the pouch 202. Once the device 100 is taken out of the pouch 202, the detected voltage would be zero. Therefore, the device 100 may check if the detected voltage across the pair of second conductors 104 is zero, as shown at step 618, and if it is so, the device 100 may go back to sleep mode, as shown at step 620.

In an embodiment, the device 100 may be calibrated to indicate extent of wetness, wherein calibration may be done by recording voltage across the second pair of first conductors when the article is dry, and recording the voltage again after soaking the article in water. The difference between the two extreme values may be stored in the host and used to indicated extent of wetness.

Figure 7:
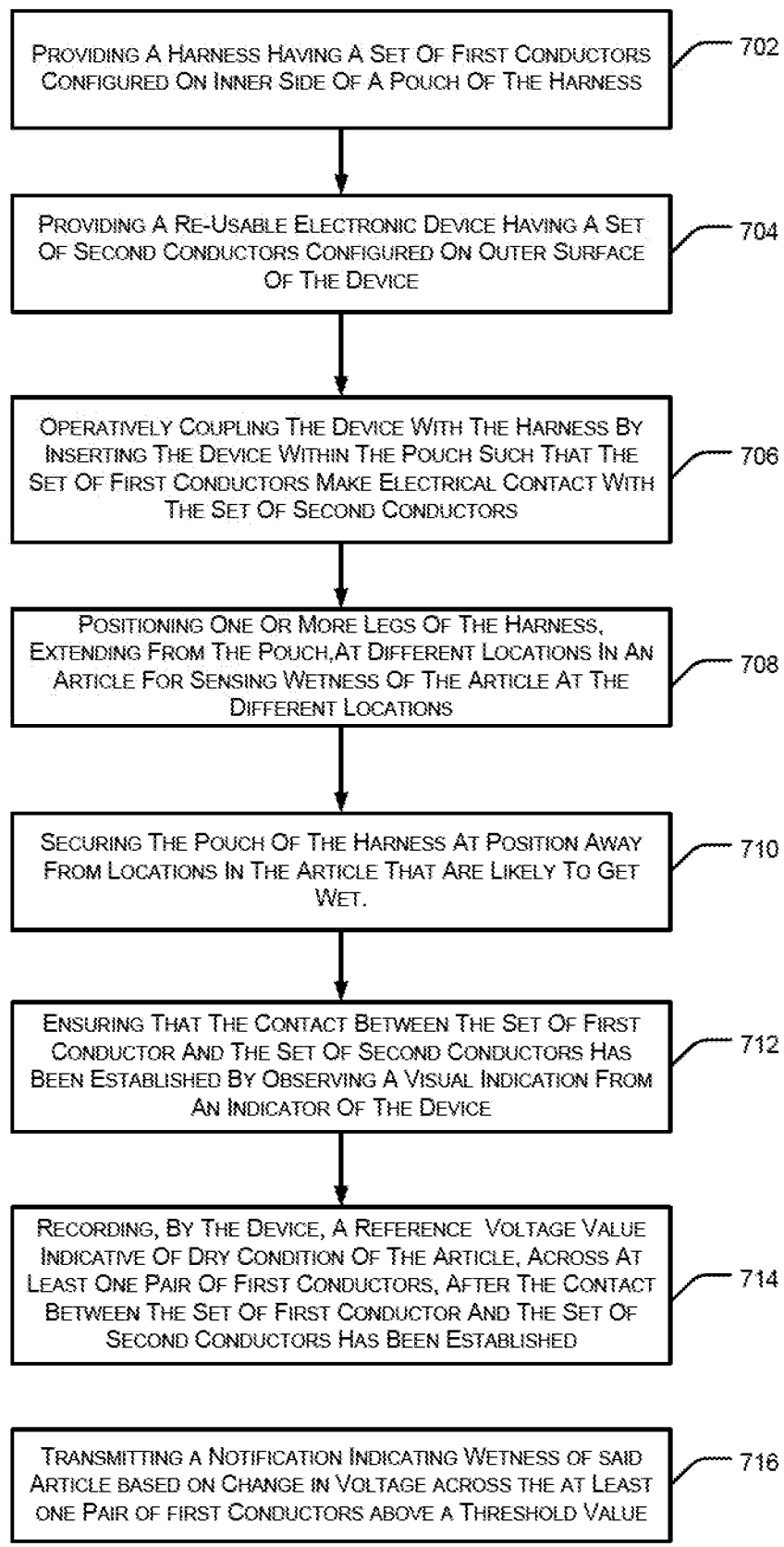
FIG. 7 is an exemplary flow diagram block diagram for the proposed method of remote monitoring of condition of an article using the proposed re-usable electronic device and the harness, according to the embodiments herein.

FIG. 7, with reference to FIGS. 1 to 6, shows various steps involved in the proposed method of remote monitoring of condition of an article using the proposed re-usable electronic device and the harness. The method of remote monitoring of condition of an article includes at step 702, providing a harness, such as harness 200 shown in FIG. 2, having a set of first conductors, such as first conductors 206 shown in FIG. 2, configured on at least one inner side of a pouch, such as pouch 202 shown in FIG. 2, of the harness 200. Step 704 of the method is to provide a re-usable electronic device, such as device 100 shown in FIG. 1 and FIG. 5, having a set of second conductors, such as second conductors 104 shown in FIG. 1, configured on outer surface of the device 100. At step 706, the device 100 may be operatively coupled with the harness 200 as shown in FIGS. 2A and 2B, by inserting the device 100 within a pouch 202 of the harness 200 such that the set of first conductors 206 make electrical contact with the set of second conductors 104. Step 708 of the method may be positioning one or more legs, such as legs 208 shown in FIG. 2, of the harness 200, extending from the pouch 202, at different locations in an article, such as the diaper 302 shown in FIG. 3, for sensing wetness of the diaper/article 302 at the different locations. At step 710, the pouch 202 may be secured at a position away from locations in the article 302 that are likely to get wet. This ensures that the device 100 does not get soiled, and therefore can be reused without any concerns of hygiene.

In an aspect, it may be ensured at step 712 that contact between the set of first conductor 206 and the set of second conductors 104 has been established. This can be ensured by observing a visual indication from an indicator, such as indicator 304 shown in FIG. 3B, of the device 100, which lights up on the contact being established. Subsequent to the contact between the set of first conductor 206 and the set of second conductors 104, at step 714, the device 100 may record a reference voltage value that is indicative of dry condition of the article 302. This may be done by applying a preset voltage across at least one pair of first conductors 206. Thereafter, voltage across the at least one pair of first conductors 206 may be periodically checked, and at step 716 of the method, if change in voltage across the at least one pair of first conductors 206 is found to be above a threshold value, a notification indicating wetness of said article may be issued through a transceiver, such as transceiver 504 of the device 100 shown in FIG. 5.

The foregoing description of the specific embodiments will so fully reveal the general nature of the embodiments herein that others may, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein may be practiced with modification within the spirit and scope of the appended claims.

What is claimed is:

1. A re-usable electronics device detachably coupled with a harness, said harness having physical connectivity with an article whose wetness condition is to be detected, said harness comprising a set of first conductors, wherein said re-usable electronics device comprises a set of second conductors such that when the re-usable electronics device is operatively coupled with the harness, the set of first conductors make electrical contact with the set of second conductors such that change in voltage across at least one pair of the first conductor above a threshold value transmits a notification indicating wetness of said article;
wherein said harness comprises a pouch in which said device is positioned for operatively coupling with the harness; and
wherein the second set of conductors of the device comprise at least two conductors located on opposite sides of the device, and wherein the first set of conductors of the harness comprises at least two conductors located on opposite inner surfaces of the pouch.

2. The device of claim 1, wherein said harness comprises a first leg coupled at rear end of said article, and a second leg coupled at front end of said article, said harness being any or a combination of a fabric, and a paper that is embedded with one or more conductive paths.

3. The device of claim 1, wherein said article is selected from any or a combination of a diaper, a sanitary napkin, and a bandage.

4. The device of claim 1, wherein the device comprises a visual indicator that is configured to indicate said electrical contact.

5. The device of claim 1, wherein said notification is transmitted by said re-usable electronics device to a remotely located computing device, said computing device being selected from any or a combination of a mobile phone, a smart phone, a laptop, a desktop PC, a server, and a wirelessly connected computing device.

6. The device of claim 1, wherein the set of first conductors is connected with a plurality of wetness sensors, said plurality of wetness sensors, upon detecting wetness of the article beyond a defined limit, being configured to enable change in voltage across the at least one pair of first conductors, said change in voltage being greater than said threshold value.

7. The device of claim 6, wherein said set of first conductors are connected with the plurality of wetness sensors through conducting paths that are painted on the harness, said painting being done by a conductive ink.

8. The device of claim 6, wherein the plurality of wetness sensors comprise four wetness sensors, and said device comprises a Wheatstone bridge such that when the first conductors and the second conductors establish the electrical contact, said four wetness sensors are configured as four sides of the Wheatstone bridge for detecting change in resistance of any one of the four wetness sensors.

9. The device of claim 6, wherein the plurality of wetness sensors comprise at least one resistance based wetness sensors.

10. The device of claim 1, wherein upon issuance of the notification, the device is detached from said harness for reuse with a fresh harness that is coupled to a second article.

11. The device of claim 1, wherein said notification is indicative of any or a combination of wetness of said article, timestamp of said notification, whether said article is soiled, dryness of said article, level of wetness of said article, and condition of said article.

12. The device of claim 1, wherein said harness is operatively coupled with at least one piezo electric material that when compressed changes capacitance or resistance or frequency of a signal passing through it, based on which the voltage across the at least a first conductor of the first set of conductors and the at least a corresponding second conductor of the second set of conductors changes so as to enable the device to transmit the notification when the voltage change is above the threshold value.

13. A harness having physical connectivity with an article whose wetness is to be measured, said harness being configured to hold a re-usable electronics device that is detachably coupled thereto, wherein said harness comprises a set of first conductors, and wherein said re-usable electronics device is operatively coupled with a set of second conductors such that when the re-usable electronics device is operatively coupled with the harness, the set of first conductors make electrical contact with the set of second conductors such that change in voltage across at least one pair of the first conductor of the first set of conductors above a threshold value transmits a notification indicating wetness of said article;
wherein said harness comprises a pouch in which said device is positioned for operatively coupling with the harness; and
wherein the second set of conductors of the device comprise at least two conductors located on opposite sides of the device, and wherein the first set of conductors of the harness comprises at least two conductors located on opposite inner surfaces of the pouch.

14. A method for remotely monitoring wetness of an article, comprising the steps of:
providing a harness having a set of first conductor configured on at least one inner side of a pouch of the harness;

providing a re-usable electronic device having a set of second conductors configured on outer surface of the device;

operatively coupling the device with the harness by inserting the device within a pouch of the harness such that the set of first conductors make electrical contact with the set of second conductors; and transmitting, by the device, a notification indicating wetness of said article based on change in voltage across at least one pair of first conductors above a threshold value, wherein the detection in change in voltage is enabled by electric contact between the set of first conductors with the set of second conductors.

15. The method of claim 14 comprising: positioning one or more legs of the harness extending from the pouch at different locations in the article for sensing wetness of the article at the different locations, wherein the at least one leg comprises a wetness sensor operatively coupled to the at least one pair of first conductors through a pair of conductive path configured on the at least one leg.

16. The method of claim 14 comprising: securing the pouch of the harness at position away from locations in the article that are likely to get wet.

17. The method of claim 14 comprising: ensuring that the contact between the set of first conductor and the set of second conductors has been established by observing a visual indication emitted by an indicator configured with the device.

18. The method of claim 14 comprising: recording, by the device, a reference voltage value across the at least one pair of first conductors after the contact between the set of first conductors and the set of second conductors has been established, wherein the reference voltage value is indicative of dry condition of the article, and the reference voltage value is taken as reference for detecting said change in voltage across the at least one pair of first conductors.

* * * * *